United States Patent [19]

Möller et al.

[11] 4,263,141

[45] Apr. 21, 1981

[54] PROCESS OF PRODUCING GASOLINE FROM SYNTHESIS GAS

[75] Inventors: Friedrich Möller, Friedrichsdorf; Friedemann Marschner, Oberursel; Emil Supp, Dietzenbach; Walter Boll, Bergen-Enkheim; Gerhard Cornelius, Karben, all of Fed. Rep. of Germany

[73] Assignee: Metallgesellschaft Aktiengesellschaft, Frankfurt am Main, Fed. Rep. of Germany

[21] Appl. No.: 85,173

[22] Filed: Oct. 15, 1979

[30] Foreign Application Priority Data

Oct. 26, 1978 [DE] Fed. Rep. of Germany ....... 2846693

[51] Int. Cl.$^3$ .......................... C07C 1/00; C07C 1/04; C07C 27/06
[52] U.S. Cl. .................................. 260/450; 260/449.5; 585/310; 585/319; 585/357; 585/469; 585/638; 585/733
[58] Field of Search ............... 260/449.5, 449 R, 450; 585/310, 319, 469, 638, 733, 357

[56] References Cited

U.S. PATENT DOCUMENTS

| | | | |
|---|---|---|---|
| 3,894,102 | 7/1975 | Chang et al. | 260/449 R |
| 3,897,471 | 7/1975 | Herbert et al. | 260/449.5 |
| 3,962,300 | 6/1976 | Hiller et al. | 260/449.5 |
| 4,011,275 | 3/1977 | Zahner | 260/449.5 |
| 4,046,830 | 9/1977 | Kuo | 260/450 |
| 4,048,250 | 9/1977 | Garwood et al. | 260/450 |
| 4,058,576 | 11/1977 | Chang et al. | 208/135 |
| 4,138,442 | 2/1979 | Chang et al. | 260/450 |

*Primary Examiner*—Howard T. Mars
*Attorney, Agent, or Firm*—Sprung, Felfe, Horn, Lynch & Kramer

[57] ABSTRACT

A process for the catalytic production of gasoline hydrocarbons from synthesis gas comprising carbon oxides and hydrogen is disclosed wherein the synthesis gas is fed initially to a methanol synthesis and thereafter effluent from the methanol synthesis is converted to gasoline hydrocarbons in a gasoline synthesis stage. The invention resides in that the entire effluent from the methanol synthesis stage is fed to the gasoline synthesis stage and at least a portion of the residual gases from the gasoline synthesis stage comprising carbon oxides, hydrogen, methane and minor amounts of $C_2$-$C_4$ hydrocarbons is fed to the methanol synthesis stage together with fresh synthesis gas.

4 Claims, 1 Drawing Figure

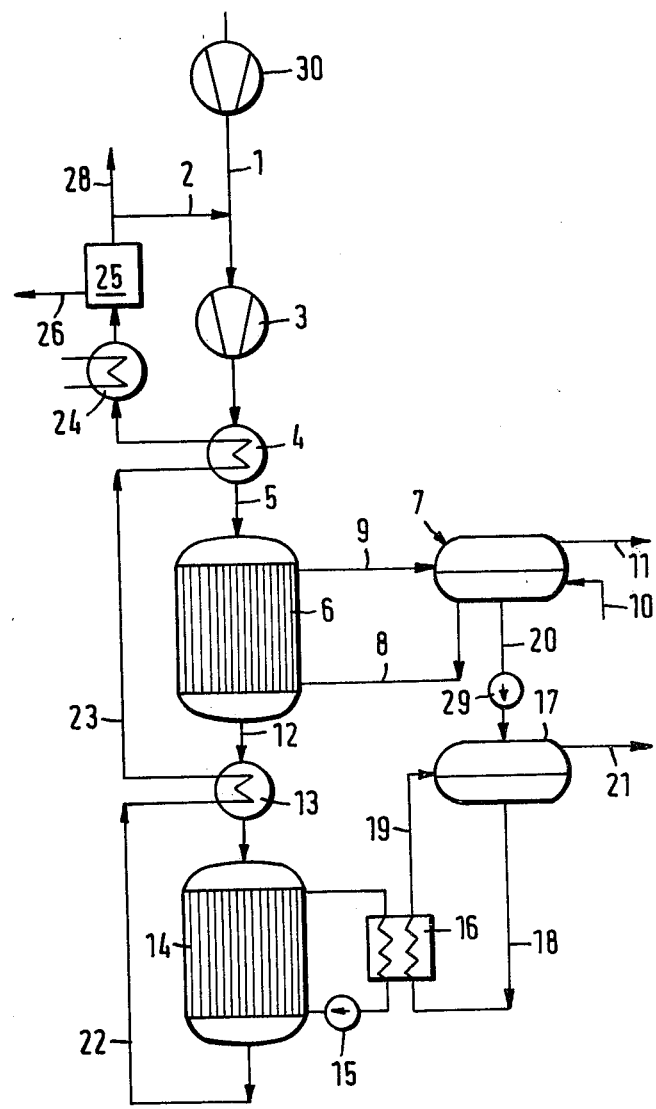

PROCESS OF PRODUCING GASOLINE FROM SYNTHESIS GAS

BACKGROUND OF THE INVENTION

1. Field of the Invention

This invention relates to a catalytic process of producing gasoline hydrocarbons ($C_5+$) from a synthesis gas which consists mainly of carbon oxides and hydrogen and which is subjected to methanol synthesis first and to gasoline synthesis thereafter.

2. Discussion of Prior Art

Such processes are known from U.S. Pat. Nos. 4,011,275; 4,048,250; and 4,058,576. In such processes, methanol and water are condensed from the effluent gas from the methanol synthesis reactor and part of the remaining effluent gas is then recycled to the synthesis stage. That recycled gas contains carbon oxides, hydrogen and methane and in a mixture with fresh synthesis gas is fed to the methanol synthesis stage. Residual gases become available also in the gasoline synthesis stage, separately from the methanol synthesis stage, and contain gaseous hydrocarbons and must also be separated and re-used in the process.

It is an object of the invention to carry out the known processes in a simple manner at low cost.

SUMMARY OF THE INVENTION

This is accomplished according to the invention in that the entire product of the methanol synthesis stage is fed to the gasoline synthesis stage, the product of the gasoline synthesis stage is cooled and gasoline hydrocarbons are removed from said product. A major part of the residual gas consisting of carbon oxides, hydrogen, methane and small amounts of gaseous hydrocarbons of the $C_2$ to $C_4$ range is fed together with fresh synthesis gas to the methanol synthesis stage. The required recycling of residual gas is affected only from the outlet of the gasoline synthesis stage to the inlet of the methanol synthesis stage.

The catalyst for the synthesis of methanol is desirably maintained at temperatures of 200° to 300° C. by an indirect cooling by means of boiling water under a pressure of 15 to 90 bars. Methanol is usually synthesized under a pressure in the range from 30 to 100 bars. The synthesis of methanol can be effected in known manner, e.g., as described in U.S. Pat. Nos. 3,962,300 and 3,959,972.

Known copper catalyst may be used in the synthesis of methanol. The catalysts may consist, e.g., of 40 to 60 atomic percent of copper, 10 to 20 atomic percent of vanadium and 20 to 50 atomic percent of zinc and/or manganese. A preferred catalyst consists of copper oxide, zinc oxide and vanadium pentoxide and before use is activated by a reduction with hydrogen. On this catalyst, the gaseous hydrocarbons of the $C_2$ to $C_4$ range in the recycled effluent gas of the gasoline synthesis stage are not reacted. This is desirable for the subsequent synthesis of gasoline. A de-activation of this catalyst for methanol synthesis by the gaseous hydrocarbons has not been observed.

The gasoline synthesis stage is operated in most cases at temperatures of 250° to 400° C., which are controlled by an indirect cooling of the reaction zone. Owing to the high temperatures, boiling water cannot be used for cooling so that higher-boiling cooling fluids or molten salts are used as cooling fluids.

Part of the boiler feed water from the steam reservoir of the methanol synthesis stage is suitably subjected to an indirect heat exchange with the cooling fluid used in the gasoline synthesis stage. Steam under a high pressure above 100 bars can be generated in this way.

The synthesis gas for use in the process according to the invention can be produced in known manner, provided that the synthesis gas contains at least 88% by volume of carbon oxides and hydrogen and that the volume ratio of $H_2$ to ($2 CO + 3 CO_2$) is at least 1. Such synthesis gas can be produced by a catalytic or thermal cracking of gaseous or liquid hydrocarbons in the presence of oxygen and/or water vapor. By a gasifying treatment of coal with oxygen and water vapor, a raw gas can be produced and this gas can be purified and may have to be shift-converted to produce the desired synthesis gas. Suitable processes of gasifying coal have been described in U.S. Pat. Nos. 4,056,483 and 3,937,620 and in the British Pat. No. 1,512,677, which the disclosures are hereby incorporated by reference.

DESCRIPTION OF SPECIAL EMBODIMENT

A possible mode of carrying out the process will be explained with reference to the drawing.

Fresh synthesis gas is supplied by a compressor 30 in conduit 1 and is mixed with hydrocarbon-containing residual gas from conduit 2. The mixed gas is compressed in the circulating compressor 3 and is heated to temperatures of about 200° to 250° C. in the heat exchanger 4.

From conduit 5, the heated gas enters a methanol synthesis reactor 6. In the tubular reactor 6, the catalyst is contained in tubes, which are surrounded by boiling water. Boiling water under pressure is fed from a steam reservoir 7 via conduit 8 to the tubular reactor as a cooling fluid. The steam produced by the cooling flows back in conduit 9 to the steam reservoir. Fresh cooling water is fed to the steam reservoir 7 via conduit 10. Surplus steam is withdrawn via conduit 11.

The gaseous and vaporous effluent produced by the catalytic reaction in the methanol synthesis stage 6 leaves the latter in conduit 12 and is heated in a heat exchanger 13 to the inlet temperature of the succeeding gasoline synthesis stage 14. That inlet temperature is usually in the range of 250° to 450° C. In the gasoline synthesis stage, the reaction takes place on known zeolite catalysts, which are indirectly cooled for a dissipation of surplus heat. The gasoline synthesis stage 14 may consist of one or more tubular reactors.

The gasoline synthesis stage 14 comprises a cooling circuit for a liquid cooling fluid. That circuit includes a circulating pump 15 and a heat exchanger 16. In the heat exchanger 16, the cooling fluid delivers heat to boiling water under pressure, which has been supplied from the steam reservoir 17. That water is fed by natural circulation in conduit 18 to the heat exchanger 16 and the generated steam flows back in conduit 19 to the steam-collecting vessel 17. The steam reservoir 17 is connected to the steam reservoir 7 by a conduit 20, which incorporates a pump 29. High-pressure steam can be taken from the steam reservoir 17 via conduit 21.

The gaseous and vaporous effluent from the gasoline synthesis stage 14 is withdrawn in conduit 22 and cooled in stages. The first cooling is effected in the heat exchanger 13. The effluent is then fed in conduit 23 to the heat exchanger 4 and is subsequently supplied to another cooler 24. In a succeeding separator 25, the valuable gasoline hydrocarbons which have now been condensed are separated; they are then withdrawn in conduit 26. At least part of the uncondensed residual gas is admixed via conduit 2 to the fresh synthesis gas in conduit 1.

Surplus residual gas is available in conduit 28 for use or for being processed. The residual gas in conduit 28 will preferably be used to produce synthesis gas because it can be used as a fuel gas and can be catalytically and/or thermally cracked into the components of the synthesis gas.

EXAMPLE

Synthesis gas having the following composition in % by volume

| | |
|---|---|
| $CO_2$ | 6.4 |
| CO | 16.2 |
| $H_2$ | 74.4 |
| $CH_4$ | 3.0 | is produced at a rate of 7.2 standard $m^3/h$ in a tubular heater, in which natural gas is cracked on a commercially available nickel catalyst in the presence of water vapor.

Residual gas from the gasoline synthesis stage, having the following composition in % by volume, is also available at a rate of 28.8 standard $m^3/h$:

| | |
|---|---|
| $CO_2$ | 2.8 |
| CO | 2.4 |
| $H_2$ | 79.8 |
| $CH_4$ | 12.6 |
| $C_2H_6$ | 0.6 |
| $C_3H_8$ | 1.1 |
| $C_4H_{10}$ | 0.7 |

In a plant as shown on the drawing, the two gases are mixed to provide 36.0 standard $m^3/h$ of a mixed gas having the following composition in % by volume:

| | |
|---|---|
| $CO_2$ | 3.5 |
| CO | 5.1 |
| $H_2$ | 78.7 |
| $CH_4$ | 10.7 |
| $C_2H_6$ | 0.5 |
| $C_3H_8$ | 0.9 |
| $C_4H_{10}$ | 0.10 |

The mixed gas is heated to 250° C. and is subjected to a methanol synthesis under a pressure of 58 bars in a tubular reactor 6, which contains 3 liters of catalyst material. The latter is cooled by boiling water under pressure. The catalyst is composed of 60 atomic percent of copper, 40 atomic per cent of zinc and 10 atomic percent of vanadium and has been produced in accordance with the specification of German Pat. No. 1,930,702 (or corresponding U.S. Pat. No.3,897,471).

The steam reservoir 7 included in the cooling system of the methanol synthesis stage is fed at a rate of 2.7 kg/h with boiler feed water preheated to 160° C. 1.5 kg/h steam under a pressure of 40 bars are withdrawn via conduit 11 at the same time.

The effluent gas from the methanol synthesis stage 6 is heated further to about 375° C. and is then reacted on the zeolite catalyst ZSM-5 in accordance with U.S. Pat. No. 4,048,250. The catalyst is contained in a tubular reactor, which is cooled with molten salt. 1.22 kg/h boiler feed water at a temperature of 250° C. and a pressure of 100 bars are fed to the steam reservoir 17 via conduit 20, which incorporates the pump 29. The same quantity of high-pressure steam at 100 bars is available in conduit 21 as a result of the heat exchange with the molten salt (conduits 18 and 19 and heat exchanger 16).

The effluent gas from the second reaction stage is cooled to the ambient temperature. As a result, 2.27 kg/h of condensible reaction products become available in two phases. These reaction products consist of 0.75 kg/h liquid gasoline hydrocarbons and 1.52 kg/h water.

Residual gas at a rate of 31.3 standard $m^3/h$ is withdrawn from the separator 25. Of this residual gas, 28.8 standard $m^3/h$ are recycled via conduit 2 and 2.5 standard $m^3/h$ are discharged via conduit 28.

The gasoline hydrocarbon product has the following composition in % by weight:

| | |
|---|---|
| Paraffins | 39 |
| Naphthenes | 15 |
| Olefins | 6 |
| Aromatic compounds | 40 |

The disclosure of all U.S., British and German patents and/or applications set forth above are hereby incorporated specifically herein by reference.

What is claimed is:

1. A process of producing gasoline hydrocarbons ($C_{5+}$) from a synthesis gas containing mainly carbon oxides and hydrogen, comprising the steps of:
   (a) feeding said synthesis gas into a methanol synthesis zone containing a methanol synthesis catalyst and producing a methanol containing product, said catalyst being indirectly cooled by boiling water under a pressure of 15 to 90 bars to maintain its temperature in the range of 200° to 300° C., said water being supplied from a first reservoir to said methanol synthesis zone and recycled to said first reservoir.
   (b) withdrawing steam from said first reservoir,
   (c) subjecting the entire methanol containing product of step (a) to a gasoline synthesis stage containing a gasoline synthesis catalyst and producing a gasoline containing product, said gasoline synthesis catalyst being indirectly cooled by a cooling liquid and maintained at a temperature of about 250° to 400° C.,
   (d) recycling said cooling liquid through an external heat exchanger zone,
   (e) withdrawing heat from said liquid in said heat exchanger zone by means of boiling water under pressure from and recycled to a second reservoir,
   (f) feeding fresh water into the first reservoir and feeding part of the boiling water from said first reservoir by a pumping means into said second reservoir, withdrawing steam with a pressure of at least 100 bars from said second reservoir.
   (g) cooling the gasoline containing product of step (c), from said product separating gasoline hydrocarbons and a residual gas comprising carbon oxides, hydrogen, methane and minor amounts of gaseous hydrocarbons of the $C_2$ to $C_4$ range, at least a portion of said residual gas being fed together with said synthesis gas into said methanol synthesis zone.

2. A process according to claim 1 wherein the product from step (c) is heat exchanged with methanol synthesis product of step (a) whereby to heat the methanol and cool the product of step (c).

3. A process according to claim 2 wherein the cooled product of step (c) after heat exchange with methanol synthesis product is further heat exchanged with the gaseous reactants being passed to the methanol synthesis stage whereby to heat said gaseous reactants and to further cool the product of step (c).

4. A process according to claim 1 wherein the methanol synthesis stage is prepared in the presence of a catalyst comprising 40 to 60 atomic percent of copper, 10 to 20 atomic percent of vanadium and 20 to 50 atomic percent of zinc and/or manganese.

* * * * *